United States Patent
Rehnberg et al.

(10) Patent No.: US 8,431,748 B2
(45) Date of Patent: Apr. 30, 2013

(54) LOW PROTONATION CONSTANT HYDROXY ACIDS

(75) Inventors: Nicola Rehnberg, Perstorp (SE); Curt Persson, Malmo (SE)

(73) Assignee: BWE I Malmo AB, Malmo (SE)

( * ) Notice: Subject to any disclaimer, the term of this patent is extended or adjusted under 35 U.S.C. 154(b) by 1152 days.

(21) Appl. No.: 12/160,760

(22) PCT Filed: Dec. 27, 2006

(86) PCT No.: PCT/SE2006/001495
§ 371 (c)(1),
(2), (4) Date: Dec. 17, 2008

(87) PCT Pub. No.: WO2007/081261
PCT Pub. Date: Jul. 19, 2007

(65) Prior Publication Data
US 2009/0155481 A1    Jun. 18, 2009

(30) Foreign Application Priority Data
Jan. 16, 2006  (SE) ...................................... 0600070

(51) Int. Cl.
C07C 61/00  (2006.01)
C07C 315/00  (2006.01)
C07C 331/00  (2006.01)
C07B 49/00  (2006.01)
C09B 59/00  (2006.01)

(52) U.S. Cl.
USPC ................. 568/31; 562/400; 568/27; 568/28; 568/32; 568/75

(58) Field of Classification Search ..................... 562/29, 562/400; 568/27, 28, 31, 32, 75
See application file for complete search history.

(56) References Cited

U.S. PATENT DOCUMENTS

| 3,959,460 | A | | 5/1976 | Vanlergerghe et al. |
| 5,470,899 | A | | 11/1995 | Gulbins et al. |
| 5,608,000 | A | | 3/1997 | Duan et al. |
| 5,665,839 | A | | 9/1997 | Rizzardo et al. |
| 5,672,662 | A | | 9/1997 | Harris et al. |
| 5,789,578 | A | * | 8/1998 | Burton et al. ................... 536/56 |
| 6,031,045 | A | | 2/2000 | Wei et al. |
| 2004/0102565 | A1 | * | 5/2004 | Maekawa et al. ............. 524/500 |

FOREIGN PATENT DOCUMENTS

| GB | 1455554 | 11/1976 |
| JP | 11228685 A1 * | 8/1999 |

OTHER PUBLICATIONS

English-language abstract of JP 11-228685 provide by Japan Patent Office.*
Machine translation of JP 11-228685 provide by Japan Patent Office.*
Oishi et al. "Smart Polyion Complex Micelles for Targeted Intracellular Delivery of PEGlyated Antisense Oligonucleotides Containing Acid-Labile Linkages," 2005, ChemBioChem, 6, 718-225.*
Oishi et al., "Smart Polyion Complex Micelles for Targeted Intracellular Delivery of PEGylated Antisense Oligonucleotides Containing Acid-Labile Linkages", ChemBioChem, 6, 718-725 (2005).
International Search Report for Application No. PCT/SE2006/001495 dated Apr. 17, 2007.
International Preliminary Report on Patentability for Application No. PCT/SE2006/001495 dated Aug. 16, 2007.

* cited by examiner

Primary Examiner — Peter F Godenschwager
Assistant Examiner — Melissa Rioja
(74) Attorney, Agent, or Firm — Knobbe Martens Olson & Bear, LLP

(57) ABSTRACT

The present invention relates to a hydroxy-sulphureous acid, to a method for preparation of the hydroxysulphureous acid and to products based on said hydroxysulphureous acid, to methods for preparation of said products and to use of said products, wherein said hydroxysulphureous acid is used as building blocks for polymer systems, e g aqueous polymer systems such as inks, coatings, and adhesives.

40 Claims, 1 Drawing Sheet

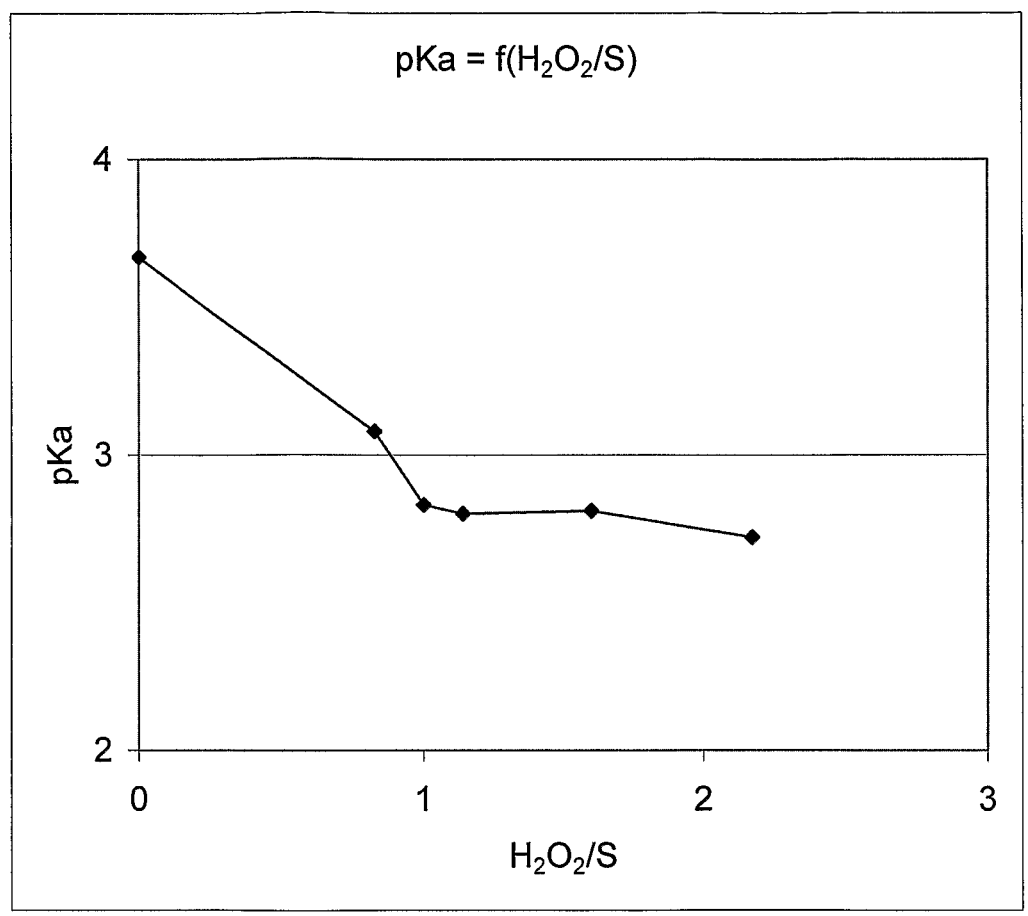

LOW PROTONATION CONSTANT HYDROXY ACIDS

CROSS-REFERENCE TO RELATED APPLICATIONS

This application is the U.S. National Phase of International Application No. PCT/SE2006/001495, filed Dec. 27, 2006, designating the U.S. and published on Jul. 19, 2007 as WO 2007/081261, which claims priority to Swedish Patent Application No. 0600070-7.

TECHNICAL FIELD OF THE INVENTION

The present invention relates to a hydroxy-sulphureous acid, to a method for preparation of the hydroxysulphureous acid and to products based on said hydroxysulphureous acid, to methods for preparation of said products and to use of said products.

BACKGROUND ART

Aqueous polymer systems such as polymer dispersions and solutions for inks, coatings, and adhesives have been known for long and usually provides excellent technical properties and high occupational safety. The polymer may be constructed from plenty of polymer building blocks, such as alcohols, acids, isocyanates, vinyl compounds and others. Many of these polymer dispersions are typically more soluble in organic solvents than in water. Due to environmental concerns, e.g. disposal of solvents, safety issues and toxicity, development of aqueous polymer dispersions have been explored during the last decade. One approach to make an aqueous polymer dispersion is to incorporate ionizable building blocks into the polymer.

However, a key component for formation of anionically stabilised polymer dispersions is a reactive anionic building block. Considering practical aspects such as availability and technical performance, the selection of products is more or less reduced to 2,2-bis(hydroxymethyl)propanoic acid, DMPA, which is a diol monocarboxylic acid, or 5-Sulfo-1,3-benzenedicarboxylic acid, SIPA. The diol functionality of DMPA provides possibility of incorporation into polymers. E.g. by reacting the diol functionality with a carboxylic acid or isocyanate to form ester or carbamate bonds, respectively.

However, DMPA has some disadvantages such as high melting point and low solubility in various solvents, that makes it hard to handle in a process. To be able to dissolve DMPA awkward solvents are used, such as N-methylpyrrolidone or acetone. Furthermore, the ionic character is provided by a regular carboxylic group. It is not activated by e.g. inductive effects, which means that it is of low acidity and has a high protonation constant, pKa, which necessitate high pH of aqueous dispersion to ionize it. Furthermore, SIPA is very difficult to use as a resin building block due to low reactivity and sulphonate based dispersion are poorly buffered and suffers from uncontrollable pH fluctuation.

GB 1,455,554 discloses anionic building blocks, e.g. diols containing sulphuric acid or sulphonate groups. These diols would, if incorporated into polymers, have favourable effects. However, there are not many existing sulphonated products available on the market, mainly due to difficulties of incorporating them into preferred systems. A problem with diols containing sulphonate groups is a need to add a buffer, when incorporated into polymer systems, to provide pH stability.

When applying a coating system of aqueous dispersion type, such as a polyurethane dispersion, based on DMPA, on a wood substrate, the pH of the top surface wood layer will shift into an unnatural region.

Wood is a very complex material composed of e.g., polycarbohydrates such as cellulose, poly(phenylpropene) structures such as lignin, resins, oils, and fatty acids. A shift of pH from natural into unnatural will affect the structures of wood giving it less desirable properties. Most notably, pH sensitive chromophores will shift colour conferring the coated wood substrate an unnatural, unattractive appearance.

EP 605,858 and U.S. Pat. No. 5,470,899 disclose a process for reducing the pH of anionic polyurethane dispersions, which are stabilized by carboxylate or sulphonate groups, by addition of compounds which have one or more ester groups.

WO 9,806,768 discloses water-based polymers and a method for the preparation of water-based sulphonated polymer composition having a pH stability of greater than 2.0. Although several systems claims to be free of organic solvents there is a need for minor amounts of organic solvents in the preparation of a prepolymer.

Many water dispersible polyesters, such as alkyds, face difficulties because the ester bonds of the polymers are subjected to degradation due to hydrolysis. The shelf life of water dispersible polymer dispersions used in the ink, coating, and adhesive industry is dependent, to a large extent, of the integrity of the ester linkage within the polymer dispersions. Cleavage of the ester bonds in polymer dispersions during storage lowers the molecular weight of the polymers and impairs the performance of the ink, coating or adhesive containing the polymer dispersion. Therefore, methods for improving the hydrolytic stability of polymer dispersions are desirable.

US2004/0152830 claims increased stability of aqueous dispersions by inclusion of hydrolytically stable ester linkages formed from secondary or tertiary hydroxyl groups. This finding is of very limited help to the polyester designer, since most of the available hydroxy building blocks are primary alcohols. The aqueous stability of esters is highly dependent on pH. The low pH of aqueous systems, made possible by the present invention, is close to optimal for restraining ester hydrolysis. Furthermore, secondary and tertiary alcohols are both of low reactivity and of low thermal and acid stability in comparison with primary alcohols.

The selection of solvents for production of polyurethane dispersions is largely limited to N-methylpyrrolidone and a few other solvents. The restrictions are imposed due, amongst other thing, to the high hydrolytic activity of high pH aqueous solutions. Ester solvents and other hydrolytically sensitive additives are normally excluded using contemporary technique.

U.S. Pat. No. 6,576,702 discloses a polyurethane dispersion where a plasticizer, such as esters, is added to the prepolymer before it is dispersed in water.

From the above mentioned references it becomes clear that there is a need for building blocks for polymer systems, e g aqueous polymer systems, that can take care of the disadvantages mentioned above, i.e. provide aqueous dispersability, stability at low pH, retention of natural wood colour, and adequate reactivity.

Therefore, it is beneficial to develop a concept for waterborne polymers with high aqueous stability, great freedom in selection of raw materials, and minimal influence on the colour of wood substrates.

SUMMARY OF THE INVENTION

The object of the present invention is to provide building blocks for polymer systems, e g aqueous polymer systems such as inks, coatings, and adhesives that provides good reactivity with other polymer building blocks, convenient handling and processing properties and stability of aqueous systems.

This object is obtained by a hydroxysulphureous acid comprising the general formula I

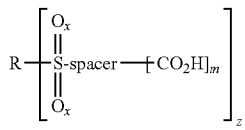

wherein z is an integer from 1 to 3,
wherein m is an integer in the range from 1 to 3,
wherein each x independently is an integer from 0 to 1,
wherein R is selected from the group consisting of:

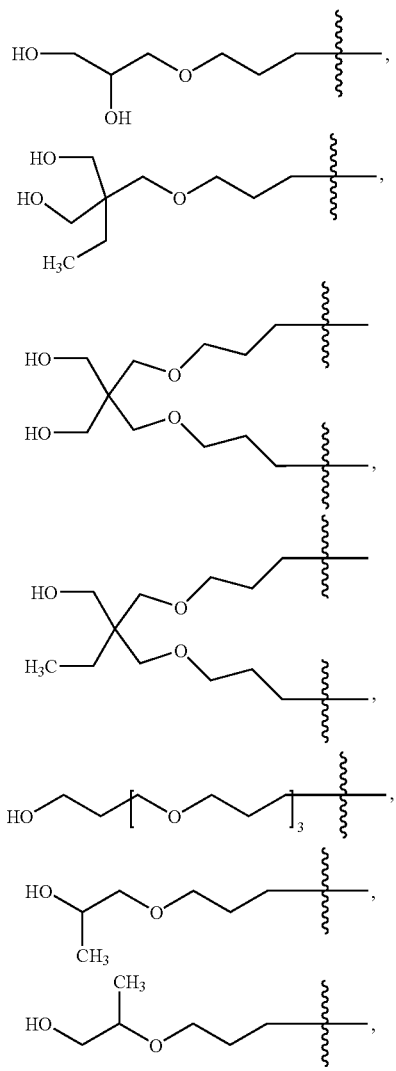

or a polymer having at least one terminal hydroxy group and a molecular weight below 2000;
wherein said spacer comprises aliphatic, linear, and/or branched, carbon rings or chains, or aromatics, optionally comprising heteroatoms selected from the group consisting of oxygen, nitrogen, sulphur or halogens; and salts of said hydroxysulphureous acid.

Another object of the invention is to provide aqueous polymer systems such that they provide attractive properties such as high hydrolytic stability, high dispersion stability at low pH, thus long shelf life, and good colour retention on wood substrates. These objects are obtained by suitable reactions of said hydroxy-sulphureous acid and other reagents, known to a person skilled in the art, to provide a product based on said hydroxysulphureous acids, which product may be an ether; a polyether; an ester; a polyester, preferably an alkyd emulsion; a urethane; a polyurethane, preferably a waterborne polyurethane; a urethane acrylate; a polyurethane acrylate; an acrylated polyurethane or acrylated polyester for radiation curing; or mixed derivatives thereof.

A specific object of the present invention is to provide methods for preparation of waterborne systems based on said hydroxysulphureous acids. This object is achieved by reacting, or incorporating, said hydroxysulphureous acid with conventional and suitable reagents, known to a person skilled in the art, to obtain e g waterborne polyurethane.

An additional object of the present invention is to provide a method for the production of hydroxysulphureous acids. This object is obtained by a method comprising:
a) providing a mercaptocarboxylic compound,
b) providing a hydroxyalkene or an epoxide,
c) reacting the mercaptocarboxylic compound with the hydroxyalkene or the epoxide, wherein said hydroxysulphureous acid is obtained,
d) optionally oxidising the sulphur atom, of the hydroxysulphureous acid, to a sulphoxide or a sulphone.

An additional object of the present invention is to provide methods for the preparation of products based on said hydroxysulphureous acid, where conventional reagents, known to a person skilled in the art, is reacted with said hydroxysulphureous acid to give an ether; a polyether; an ester; a polyester, preferably an alkyd emulsion; a urethane; a polyurethane, preferably a waterborne polyurethane; a urethane acrylate; a polyurethane acrylate; an acrylated polyurethane or acrylated polyester for radiation curing or any mixture thereof.

Another object is to provide use of the products, based on said hydroxysulphureous acid, in coating of a substrate, e g preferably wood substrates, such as wooden tile, or parquet flooring, metal substrates, leather substrates, textile substrates, cork substrates, plastic substrates, such as PVC (polyvinyl chloride) and paper substrates, wherein said product preferably is waterborne.

Yet another object of the present invention is to provide linear, and/or branched polyesters which may be acrylated, based on said hydroxysulphureous acid, for the use in preparation of an air drying alkyd resin; a 1- or 2-component polyurethane coating or adhesive; a saturated or unsaturated polyester; a toughening agent for thermosetting resins and/or composites made therefrom; a pigment dispersion agent for solvent-free, solventborne, waterborne coatings, polyolefines and thermoplastics; a water dispersible resin for alkyd emulsions, acrylic dispersions and polyurethane dispersions; a dispersing polymer or resin; a processing aid for polyolefines and thermoplastics; a concrete admixture imparting fluidity to hydraulic compositions; or a polyurethane foam. In case the linear, and/or branched polyesters are acrylated they may be used in a radiation curing coating, printing ink or adhesive.

The hydroxysulphureous acids according to the present invention are typically suitable for manufacturing of waterborne products, polyester products, such as linear, and/or branched polymers or alkyds, or polyether products, where a hydroxysulphureous acid is reacted with suitable conventional reagents to give e g a polyurethane preferably a waterborne polyurethane, a polyurethane acrylate, an acrylated polyurethane or acrylated polyester for radiation curing, a polyester, a polyether, or an alkyd.

The hydroxysulphureous acids according to the invention have the advantage that they are easy to obtain from commercially available starting materials by the method described above and in the claims. Other advantages with the hydroxysulphureous acids according to the invention are that the hydroxysulphureous acid is stabile at low pH, it may easily be converted into its anionic active form, without excessively raising the pH and it gives stabile aqueous polymer systems. This has the advantage that it may be used in waterborne polyurethanes for wood substrates, while retaining the natural pH of the wood substrates, and as such avoid that sensitive chromophores of the wood will shift colour conferring the coated wood substrate an unnatural, unattractive appearance.

Additional advantages with the hydroxysulphureous acids according to the present invention are that they are very versatile and may be used to prepare many different polymer systems, for a wide variety of applications. The hydroxysulphureous acid according to the present invention may be reacted with suitable reagents to provide a product, comprising the hydroxysulphureous acids according to the present invention, which may be an ether, a polyether, an ester, a polyester, a urethane, a polyurethane, an urethane acrylate, a polyurethane acrylate, an acrylated polyurethane or acrylated polyester for radiation curing, or mixed derivatives thereof. The hydroxysulphureous acids according to the invention may also be included in polymers used in photoresist applications, pigment pastes, adhesives, for improving dyability and in polish for wood substrates.

Another advantage of the present invention is that the hydroxysulphureous acids according to the present invention makes it possible to adjust pH of aqueous polymer systems to achieve optimal stability of ester components.

An additional advantage of the present invention is by using said hydroxysulphureous acid makes it possible to choose between several solvents in the preparation of polymer systems, such as waterborne polyurethanes.

Another advantage according to the present invention is that there is no need to add a buffer, when incorporating the hydroxysulphureous acid into polymer systems.

BRIEF DESCRIPTION OF THE DRAWINGS

FIG. 1 illustrates a graph showing the effect on pKa value of oxidation of a hydroxysulphureous acids.

DETAILED DESCRIPTION OF SPECIFIC EMBODIMENTS OF THE INVENTION

In one embodiment of the present invention a hydroxysulphureous acid comprising the general formula I

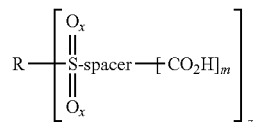

wherein z is an integer from 1 to 5, preferably 1 to 3,
wherein m is an integer in the range from 1 to 3,
wherein each x independently is an integer from 0 to 1,
wherein R is selected from the group consisting of:

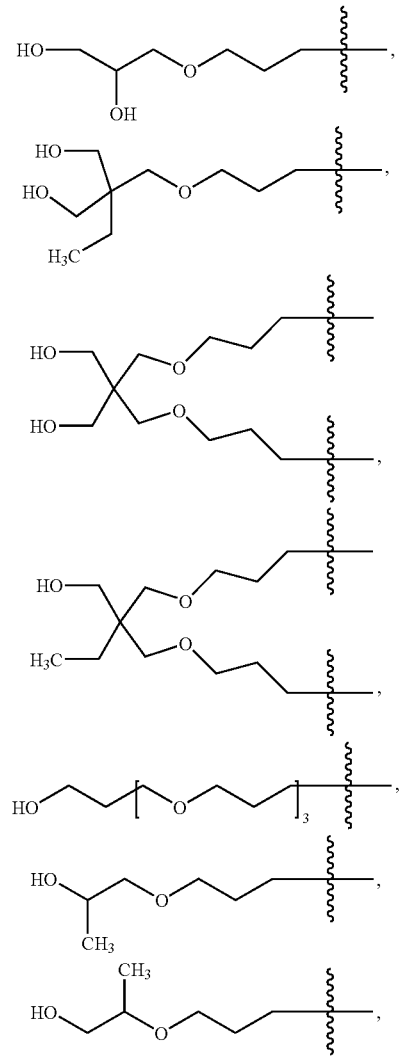

or a polymer having at least one terminal hydroxy group and a molecular weight below 2000;
wherein said spacer comprises aliphatic, linear, and/or branched, carbon rings or chains, or aromatics, optionally comprising heteroatoms selected from the group consisting of oxygen, nitrogen, sulphur or halogens; and salts of said hydroxysulphureous acid.

In formula I R may be selected as described above and has at least one binding to the other part of formula I, i e R binds to a sulphur atom. R may bind to more than one sulphur atom, which through a spacer is connected to at least one carboxylic acid group, or a carboxylate; wherein said sulphur atom, spacer and carboxylic acid group, or carboxylate constitutes the "other part" of formula I. Each

denotes a binding between R and a sulphur atom in general formula I. A non-limiting example is the general formula A:

Formula A

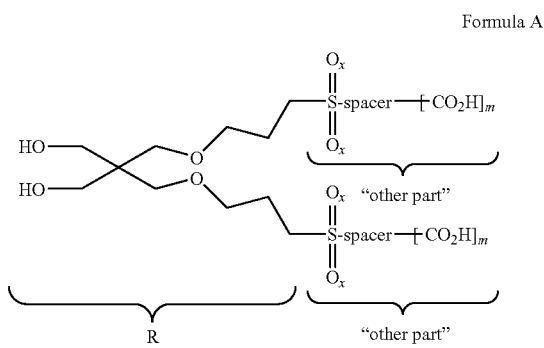

wherein X, spacer and m is as defined above
When more than one

exists in the same R group it is to be understood as more than one "other part" may be bound to the one and same R group, e g as disclosed in formula A.

Furthermore as defined above z may be 1 to 3, however z may also be more than 3, e g 4 and 5. This may for example be the case when R is a polymer.

According to the present invention a hydroxysulphureous acid means a sulphur, hydroxy and acid containing compound according to the general formula I above. According to the present invention the hydroxysulphureous acid may be obtained as a salt of any of lithium, sodium, potassium, cesium, magnesium, calcium, aluminium, ammonium, or substituted ammonium such as trimethylammonium, triethylammonium, triethanolamine, dimethylaminoethanol, N-methylmorpholine, tetrabutylammonium, or phosphonium.

The hydroxysulphureous acid may be formed by an addition reaction between a mercaptocarboxylic compound and a hydroxyalkene, or an epoxide.

In one embodiment of the present invention R is a polymer having at least one terminal hydroxy group, wherein said polymer preferably is a polyester, e.g. fatty acid ester, unsaturated ester, alkyd or propylenether polyester; or a polyether, e.g. alkoxylated propylene ether, alkoxylated polyol propylene ether, alkoxylated glycerol propylene ether.

In one embodiment of the present invention spacer is a linear or branched alkyl chain, preferably comprising 1-10 carbon atoms.

In one embodiment of the present invention said mercaptocarboxylic compound preferably is an aliphatic mercaptocarboxylic acid, such as a 2-mercaptocarboxylic acid, e.g. mercaptoacetic acid, 2-mercaptopropionic acid, 2-mercapto-2-methylpropionic acid, 2-mercaptobutyric acid, 2-mercaptopentanoic acid, 2-mercaptosuccinic acid; a 3-mercaptocarboxylic acid, 3-mercaptopropionic acid; α-mercaptocyclohexanecarboxylic acid; or 11-mercaptoundecanoic acid; or aromatic mercaptocarboxylic acid, such as ortho-, metha-, or para-mercaptobenzoic acid; or a mercaptonaphthoic acid.

In one embodiment of the present invention said hydroxyalkene is an unsaturated alcohol, preferably an allyl alcohol, such as allyl alcohol, methallyl alcohol, or 1,4-but-2-enediol; or an allyl alcohol derivative, such as an alkoxylated allyl alcohol, e.g. allyl alcohol ethoxylate such as allyl alcohol monoethoxylate, allyl alcohol diethoxylate, allyl alcohol triethoxylate, allyl alcohol oligoethoxylate, allyl alcohol polyethoxylate or any combination thereof, or an allyl alcohol propoxylate, such as allyl alcohol monopropoxylate, allyl alcohol di-propoxylate, allyl alcohol tripropoxylate, allyl alcohol oligopropoxylate, allyl alcohol polypropoxylate, or any combination thereof; or a methallyl alcohol ethoxylated; or a methallyl alcohol propoxylated; or an allyl or methallyl copoly(ethoxylate-propoxylate).

In one embodiment of the present invention the hydroxyalkene is a polyol allyl or methallyl ether, where the polyol allyl or methallyl ether are allyl- and methallyl ethers of butanediol, pentanediol, hexanediol, neopentyl glycol, trimethylolethane, trimethylolpropane, pentaerythritol, di-trimethylopropane, dipentaerythritol, anhydroenneaheptitol, 2,2,6,6-tetrakis(hydroxymethyl)cyclohexanol, 3,9-bis(2-hydroxy-1,1-dimethylethyl)-2,4,8,10-tetraoxaspiro[5.5]undecane, 3,11-bis(2-hydroxy-1,1-dimethylethyl)-2,4,10,12-tetraoxadispiro[5.1.5.3]-hexadecane-7-ol, glycerol, hexanetriol, erythritol, xylitol, arabitol, sorbitol, saccarose, methyl glucoside, hydroquinone, or resorcinol, with the proviso of perallyl ethers.

In one embodiment of the present invention the hydroxyalkene is a glycerol diallyl ether, glycerol monoallyl ether, trimethylolpropane diallyl ether, trimethylolpropane monoallyl ether, pentaerythritol triallyl ether, pentaerythritol diallyl ether, pentaerythritol monoallyl ether, ditrimethylolpropane monoallyl ether, ditrimethylolpropane diallyl ether, ditrimethylolpropane triallyl ether, 2,2,6,6-tetrakis(hydroxymethyl)cyclohexanol tetraallyl ether, 1,5-bis(hydroxymethyl)-3-oxabicyclo[3.3.1]nonan-9-ol allyl ethers or alkoxylated allyl ethers, e g alkoxylated polyol allyl ethers, alkoxylated glycerol allyl ethers.

In one embodiment of the present invention the hydroxyalkene is a fatty acid ester, or an unsaturated ester such as an alkyd or an allylether polyester.

In one embodiment of the present invention the hydroxysulphureous acid is formed by an addition reaction between a mercaptocarboxylic compound and an epoxide. Where said epoxide may be bisphenol A diglycidyl ether, limonene oxide, vinylcyclohexene oxide, diglycidyl ether, glycidyl allyl ether, a polyol glycidyl ether, glycidol or an epoxidized soybean oil.

In one embodiment of the present invention the mercaptocarboxylic compound is a mercaptosulphureous acid, such as 2-mercaptoethylsulphonic acid or o-, m-, or p-mercaptobenzenesulphonic acid.

In one embodiment of the present invention said hydroxysulphureous acid is formed by an addition reaction between a thiocarboxylic acid such as thioacetic acid, thiopropinoic acid, or thiobenzoic acid, and a hydroxyalkene or an epoxide, optionally followed by oxidation and hydrolysis of the intermediary S-(hydroxyalkyl)thiocarboxylic ester.

In one embodiment of the present invention the sulphur atom in said hydroxysulphureous acid is oxidised to a sulphone or sulphoxide by an oxidising agent, such as air, oxygen, hydrogen peroxide, peracetic acid, permaleic acid, perbenzoic acid, t-butyl hypochlorite, sodium perborate, potassium hydrogen persulfate, or ammonium peroxodisulfate.

In one embodiment of the present invention a method for the preparation of the hydroxysulphureous acid is provided. The method comprises provision of a mercaptocarboxylic compound and a hydroxyalkene or an epoxide, reacting said mercaptocarboxylic compound with said hydroxyalkene or said epoxide, whereby said hydroxysulphureous acid is obtained, and optionally oxidising the hydroxysulphureous acid to sulphoxide or sulphone by the use of an oxidising agent, as defined above, in any further process step. The effect of oxidation is illustrated in FIG. 1, oxidation provides a mean of increasing acid strength. In said method the mercaptocarboxylic compound or a salt thereof may be added, in an excess, equivalence or deficit amounts, to the hydroxyalkene or epoxide or the hydroxyalkene or epoxide may be added, in an excess, equivalence or deficit amounts, to the mercapto compound. The reaction temperature is from −20 to 140° C., preferably from 0 to 100° C., more preferably from 40 to 90° C., most preferred from 60 to 85° C. The reaction is run neat or in the presence of a solvent such as an alcohol, a ketone, an ester, an aromatic or a chlorinated solvent. The reaction may be done in the presence of an initiator such as bis-azoisobutyronitrile, benzoyl peroxide, t-butyl hydroperoxide, cumene hydroperoxide, oxygen, or air or where the reaction mixture is initiated by irradiation with electromagnetic radiation such as UV light or electron beam. If a catalyst is present the amount of initiator of the total mass of reactants is from 0 to 3%, preferably from 0.0001 to 1%, more preferably from 0.01 to 0.75%, most preferred from 0.05 to 0.5%.

According to the present application the term "product" means an ether; a polyether; an ester; a polyester, preferably an alkyd emulsion; a urethane; a polyurethane, preferably a waterborne polyurethane; a urethane acrylate; a polyurethane acrylate; an acrylated polyurethane or acrylated polyester for radiation curing or any mixture thereof, which is based on the hydroxy-sulphureous acid according to the present invention.

According to the present invention the term "acrylate" means a compound that has been acrylated with any one of acrylic acid, acrylic ester, methacrylic acid and methacrylic ester.

In one embodiment of the present invention said hydroxysulphureous acid is reacted with a suitable reagent(s), such as conventional reagents used in etherification reactions, known to a person skilled in the art, where a product, such as an ether or polyether is obtained. A suitable reagent may be an alkylene oxide.

In one embodiment of the present invention said hydroxysulphureous acid is reacted with a suitable reagent(s), such as conventional reagents used in esterification reactions, known to a person skilled in the art, where a product, such as an ester or polyester, preferably an alkyd, is obtained. A suitable reagent may be a carboxylic acid or a lactone such as caprolactone.

In one embodiment of the present invention said hydroxysulphureous acid is reacted with a suitable reagent(s), where a product, e g a urethane or polyurethane is obtained. Where the polyurethane may be a waterborne polyurethane.

In one embodiment of the present invention said hydroxysulphureous acid is reacted with a suitable reagent(s), where a product, such as a urethane acrylate, or a polyurethane acrylate is obtained by addition of an acrylic ester or methacrylic ester, followed by polymerization of the ester, either to a method for preparation of a urethane, e g as a solvent, or to a urethane or a polyurethane. Where the polymerization of the acrylic ester or methacrylic ester may be done by any conventional radical polymerization system, e g thermally induced polymerization or redox polymerization systems. Said urethane acrylate or polyurethane acrylate may be used in a coating, printing ink or adhesive.

In one embodiment of the present invention said hydroxysulphureous acid is reacted with an acrylated polymer and other suitable reagents, known to a person skilled in the art, such as acrylic acid, acrylic ester, methacrylic acid or methacrylic ester, or an isocyanate, where a product such as an acrylated polyurethane or an acrylated polyester for radiation curing, is obtained. Said acrylated polyurethane or acrylated polyester is used in a radiation curing coating, printing ink or adhesive.

The above mentioned products are used in coating of a substrate, preferably wood substrates, metal substrates, leather substrates, textile substrates, plastic substrates and paper substrates.

In one embodiment of the present invention a method for the preparation of a polyurethane product comprising reacting:

a) an isocyanate or an isocyanate mixture such as hexane diisocyanate, toluene diisocyanate, isophorone diisocyanate, naphthalene diisocyanate, 4,4'-dicyclohexylmethane diisocyanate, 4,4'-diphenylmethane diisocyanate, tetramethyl xylylene diisocyanate, trimethylhexamethylene diisocyanate or dimers, trimers or oligomers thereof b) a polyol such as low molecular weight polyols such as ethylene glycol, diethyleneglycol, oligoethyleneglycols, propyleneglycol, dipropyleneglycol, oligopropyleneglycols, butyleneglycol, pentyleneglycol, hexyleneglycol, decanediol, dodecanediol, reduced dimer acid diols, fatty acid polyols such as ricinoleic acid derivatives, epoxidised oil polyol derivatives, glycerol, neopentylic polyols such as neopentyl glycol, hydroxypivalyl hydroxypivalate, 2-butyl-2-ethylpropanediol, trimethylolethane, trimethylolpropane, pentaerythritol, dipolyols such as dineopentylglycol, ditrimethylolpropane, dipentaerythritol, 2,2,6,6-tetrakis(hydroxymethyl)cyclohexan-1-ol, alkoxylated neopentyl polyols such as ethoxylated or propoxylated neopentyl glycol, trimethylolpropane, ditrimethylolpropane, dipentaerythritol, 2,2,6,6-tetrakis(hydroxymethyl)cyclohexan-2-ol, polyether polyols such as polyethyleneoxide, polypropylene oxide, polytetrahydrofurane, polycarbonate polyols such as poly(1,4-butandiol carbonate), poly(1,6-hexanediol carbonate), poly(2-butyl-2-ethyl-1,3-propandiol carbonate), poly(neopentylglycol carbonate), poly(bisphenol A carbonate), polylactone polyols such as polycaprolactone; polyester polyols prepared from alcohols such as ethyleneglycols, diethylene glycol, propyleneglycol, dipropylenglycol, butanediol, pentanediol, hexanediol, cyclohexanedimethanol, decanediol, dodecanediol, neopentylic polyols such as neopentyl glycol, hydroxypivalyl hydroxypivalate, 2-butyl-2-ethylpropanediol, trimethylolpropane, pentaerythritol, bis(4-hydroxycyclohexane)methane, and an acid such as succinic acid, glutaric acid, adipic acid, cyclohexanedicarboxylic acid, decanedicarboxylic acid, dodecane dicarboxylic acid, orthophthalic acid or anhydride, isophthalic acid, terephthalic acid, trimellitic acid, pyromellitic acid, dihydrophthalic acid, tetrahydrophthalic acid, maleic anhydride, fumaric acid, and, optionally, a monocarboxylic acids such as benzoic acid, acrylic acid, methacrylic acid, t-butylbenzoic acid, 2-ethylhexanoic acid, plant or animal derived acids in pure or natural mixtures, in trans or otherwise rearranged forms, such as octanoic acid, palmitic acid, stearic acid, oleic acid, linoleic acid, linolenic acid, and silicone diols, such as Silicone Fluid OH 15D, available from Wacker Chemie AG;

c) a hydroxysulphureous acid according to the general formula above or a mixture thereof, optionally in mixture with 2,2-bis(hydroxymethyl)propanoic acid, 2,2-bis(hydroxymethyl)butanoic acid or hydroxypivalic acid, d) optionally in the presence of a catalyst or a mixture of catalysts, such as a tin compound or an amine, or a phosphoric acid or a phosphate e) optionally in the presence of a solvent or a solvent mixture, such as a lactame for example N-methylpyrrolidone, N-ethylpyrrolidone, vinylpyrrolidone or vinylcaprolactame, such as an alcohol, for example t-butanol or diacetone alcohol, an ester such as caprolactone, ethylene carbonate, propylene carbonate, ethyl formate, ethyl acetate, butyl propionate, isobutyl isobutyrate, ethyleneglycol diacetate, propylenglycol diacetate, dimethyl succinate, dimethyl glutarate, propyl acrylate, butyl acrylate, ethylene glycol diacrylate, methylhexamethylglycol acrylate, methyl methacrylate, ethyl methacrylate, triethylene glycol dimethacrylate, acetoacetoxyethyl methacrylate, or an ether such as diisopropyl ether, ethyleneglycol dimethyl ether, diethyleneglycol dimethyl ether, triethyleneglycol dimethyl ether, propylene glycol dimethyl ether, dipropyleneglycol dimethyl ether, tripropyleneglycol dimethyl ether, or an amide such as diacetoneacrylamide, tert-butylacrylamide or N-acetylmorpholine, or vinylsilanes, such as trimethoxy vinylsilane.

f) optionally in the presence of additives such as siccatives, surface modifying agents, optical appearance modifying agents, UV adsorbents, g) optionally in the presence of a neutralising base such as an amine or a mixture thereof, e.g. triethyl amine, N-methylmorpholine, N,N-dimethylaminoethanol, or a salt such as sodium hydroxide or potassium carbonate, h) a chain extending nitrogen compound such as ethylenediamine, propylenediamine, butylenediamine, pentylenediamine, hexylenediamine, diethylenetriamine, isophorondiamine, hydrazine, adipic acid dihydrazide, amino polyalkylene oxide, or a mixture thereof, i) optionally an oxidizing agent is added, j) optionally a pH adjuster is added, is provided, where conventional reaction parameters, known to a person skilled in the art may be used, e g as described in Polyurethanes for Coatings, M. Bock, Vinzentz Verlag, Hanover, ISBN 3-87870-732-0 and references included therein. Within said method a), b), c), d), e), f) and g) may be added in any order, if present, and will result in a prepolymer. The prepolymer is mixed with water, followed by addition of a chain extending compound according to h) and optionally followed by i) and j).

In one embodiment of the present invention said hydroxysulphureous acid is used to prepare a linear, and/or branched polyester, which may be prepared by homocondensation of the hydroxysulphureous acid, or co-condensation of the hydroxysulphureous acid with a carboxylic acid such as hydroxypivalic acid, lactic acid, 6-hydroxyhexanoic acid, 2,2-bis(hydroxymethyl)propionic acid, 2,2-bis(hydroxymethyl)butanoic acid, or a mixture thereof, optionally including an alcohol, e.g. methanol, ethanol, propanol, butanol, pentanol, hexanol octanol, dodecanol, hexadecanol, octadecanol, 2-ethylhexanol, ethylene glycol, neopentyl glycol, hydroxypivalyl hydroxypivalate, glycerol, trimethylolethane, trimethylolpropane, pentaerythritol, di-trimethylolpropane, dipentaerythritol, or alkoxylated polyols, where the homocondensation or the co-condensation optionally includes a catalyst, e.g. an acid such as p-toluenesulphonic acid or a tin compound such as butylstannoic acid, and where the obtained product optionally is chain extended, chain terminated and/or functionalised, and where the obtained linear, and/or branched polyester is used in, or for the preparation of:

a) an air drying alkyd resin,
b) a 1- or 2-component polyurethane coating or adhesive,
c) a saturated or unsaturated polyester,
d) a toughening agent for thermosetting resins, such as an epoxy resins, unsaturated polyesters, vinyl esters, polyurethanes, maleimides, cyanate esters, phenolics/urea-formaldehyde resins and melamine-formaldehyde resins, and/or composites made therefrom,
e) a pigment dispersion agent for solvent-free, solventborne, waterborne coatings, polyolefines and thermoplastics, such as polycarbonates, polyamides, polyesters, polyimides and polyurethanes,
f) a water dispersible resin for alkyd emulsions, acrylic dispersions and polyurethane dispersions,
g) a dispersing polymer or resin, such as a reactive polymeric surfactant, for alkyds, polyesters, polyethers and polyurethanes,
h) a processing aid for polyolefines and thermoplastics, such as polycarbonates, polyamides, polyester, polyimides and polyurethanes,
i) a concrete admixture imparting fluidity to hydraulic compositions, such as cement pastes, mortars or concretes,
j) a polyurethane foam.

Said linear, and/or branched polyester may be acrylated by reagents such as acrylic acid, acrylic ester, methacrylic acid and methacrylic ester to give a product that may be used in a radiation curing coating, printing ink or adhesive.

EXAMPLES

As used herein AIBN means azobisisobutyronitrile, KOH means potassium hydroxide, Fe-EDTA means an iron complex of ethylenediaminetetraacetic acid (EDTA)

Example 1a

Synthesis of a Glycerol Monoallyl Ether-Thiolactic Acid Adduct, GALA

AIBN (3.5 g) was dissolved in glycerol monoallyl ether (894 g, 6.77 mol). This solution was slowly added, under nitrogen with stirring, to thiolactic acid (718 g, 6.77 mol) at such a rate that the temperature of the exothermal reaction was kept at 85° C. When the addition was completed, the temperature was raised to 90° C. and kept at 90° C. for 1 h. The product had $^1$H-NMR (CDCl$_3$): δ 1.42 (d, 3H, J=7 Hz, SCHCH$_3$), 1.78-1.98 (m, 2H, CH$_2$CH$_2$CH$_2$), 3.65-3.92 (m, 2H, CH$_2$S), 3.38-3.78 (m, 7H), 3.85-3.95 (m, 1H); and is soluble in water, methanol, ethanol/toluene (¼), not soluble in hexane.

Example 1b

Air Promoted Addition of Thiolactic Acid To Glycerol Monoallyl Ether, GALA

Thiolactic acid (133.7 g) was added to a reaction flask equipped with an efficient stirring propeller and heated to 90° C. Triethylamine (6.4 g) was added, air was passed thru the flask and glycerol monoallyl ether was added at such a rate to keep the temperature at 90° C. When the addition was completed, the reaction was allowed to proceed at 90° C. for 3.5 h to give the title adduct.

Example 2

Synthesis of a Trimethyolpropane Monoallyl Ether-Thiolactic Acid Adduct, TELA

AIBN (1.5 g) was dissolved in trimethylolpropane monoallyl ether (497 g, 2.86 mol). This solution was slowly added, under nitrogen with stirring, to thiolactic acid (300 g, 2.83 mol) at such a rate that the temperature of the exothermal reaction was kept at 80° C. When the addition was completed, the temperature was raised to 90° C. and kept at 90° C. for 1 h. The product had $^1$H-NMR (CDCl$_3$): δ 1.11 (t, 3H, CH$_3$CH$_2$), 1.53 (q, 2H, CH$_3$CH$_2$), 2.00-2.20 (m, 2H, CH$_2$CH$_2$CH$_2$), 2.98-3.06 (m, 2H, 3.65-4.02 (m, 9H); and is soluble in methanol and toluene, not soluble in hexane.

Example 3

Synthesis of a Trimethyolpropane Diallyl Ether-Thiolactic Acid Adduct, TDELA

AIBN (100 mg) was dissolved in trimethylolpropane diallyl ether (10.08 g, 47 mmol) and the mixture was added, with stirring, to thiolactic acid (10 g, 94 mmol). The mixture was placed in an oven at 60° C. for 16 h. The product had $^1$H-NMR (CDCl$_3$): δ 0.70-0.80 (m, 3H, CH$_3$CH$_2$), 1.20-1.50 (m, 4H), 1.60-1.90 (m, 4H), 2.65-2.80 (m, 4H), 3.20-3.60 (m, 19H).

Example 4

Synthesis of a Trimethylolpropane Monoallyl Ether-Mercaptoacetic Acid Adduct, TEMA AIBN (132 mg) was dissolved in trimethylolpropane monoallyl ether (25 g, 0.14 mol) and added with stirring to mercaptoacetic acid (13.2 g, 0.14 mol). The reaction mixture was heated for 30 min at 85° C. The product had $^1$H-NMR (CDCl$_3$): δ 0.90 (t, 3H, CH$_3$), 1.37 (q, 2H, CH$_3$CH$_2$), 1.95 (m, 2H, CH$_2$CH$_2$CH$_2$), 2.80 (t, 2H, CH$_2$CH$_2$S), 3.30 (s, 2H, CH$_2$COOH), 3.50 (s, 2H, CCH$_2$OCH$_2$), 3.57 (t, 2H, CCH$_2$OCH$_2$), 3.70 (d, 2H, CH$_2$OH), 3.80 (d, 2H, CH$_2$OH).

Example 5

Synthesis of a Glycerol 1-Monoallyl Ether-Mercaptoacetic Acid, GAMA

AIBN (50 mg) was dissolved in glycerol 1-allyl ether (15 g, 0.11 mol) and added to mercaptoacetic acid (10.51, 0.11 mol) with stirring. The mixture was placed in an oven at 60° C. for 15 h. The product had $^1$H-NMR (CDCl$_3$): δ 1.93 (p, 2H, CH$_2$CH$_2$CH$_2$, J=5 Hz), 2.79 (t, 2H, CH$_2$CH$_2$CH$_2$S, J=6 Hz), 3.24/s, 2H), 3.5-3.75 (m, 6H), 3.90 (m, 1H)

Example 6

Synthesis of an Allyloxypropanol-Mercaptoacetic Acid Adduct, APMA

AIBN (100 mg) was dissolved in allyloxypropanol (10 g, 86 mmol), and added, with stirring, to mercaptoacetic acid (7.95 g, 86 mmol). The reaction mixture was placed in an oven at 60° C. for 15 h. The product had $^1$H-NMR (CDCl$_3$): δ 1.20 (d, 3H, CH$_3$), 1.95 (p, 2H, CH$_2$CH$_2$CH$_2$), 2.80 (t, 2H, CH$_2$S), 3.30 (s, 2H, CH$_2$COOH), 3.31 (d, 1H, CHOHCH$_2$), 3.45 (d, 1H, CHOHCH$_2$), 3.65 (m, 2H, OCH$_2$CH$_2$), 4.05 (m, 1H, CHOH).

Example 7

Synthesis of a Glycerol Monoallyl Ether-3-Mercaptopropanoic Acid Adduct, GAPA

AIBN (50 mg) was dissolved in glycerol 1-monoallyl ether (15 g, 0.11 mol), and added to 3-mercaptopropanoic acid (12.06, 0.11 mol) with stirring. The reaction mixture was place in an oven at 60° C. for 15 h. The product had $^1$H-NMR (CDCl$_3$): δ 1.83 (p, 2H, CH$_2$CH$_2$CH$_2$, J=5 Hz), 2.59 (m, 4H) 2.72 (t, 2H, J=6 Hz), 3.41-3.69 (m, 6H), 3.86 (p, 1H, J=4 Hz).

Example 8

Synthesis of a Short Polyester and Addition of Thiolactic Acid

Adipic acid (244 g, 1.67 mmol), trimethylolpropane monoallyl ether (674 g, 3.87 mol), and Fascat 4100 (0.6 g) were reacted with azeotropical removal of water to an acid number of 0.75 mg KOH/g. This polyester (150 g) was treated with thiolactic acid (63.1 g, 0.60 mol) and AIBN (630 mg). The mixture was stirred at 60° C. for 2 h, and then placed in an oven at 60° C. for 15 h. The product had $^1$H-NMR (CDCl$_3$): δ 1.80 (m), 2.60 (m) indicative of successful addition.

Example 9

Synthesis of a Hydroxy Terminated Branched Polyester

Mercaptoacetic acid (92.1 g, 1.0 mol) was charged to the reaction flask. AIBN (435 mg) was dissolved in trimethylolpropane monoallyl ether (174 g, 1.0 mol) and the solution was slowly added to the reaction flask to keep the temperature at 80° C. When the addition was completed, heptane was added and the temperature was raised to 130° C. The condensation was followed by collection of water and acid number titrations. The condensation was terminated when an acid number of 39 mg KOH/g was reached, corresponding to a molecular weight of 1450 g/mol.

Example 10

Synthesis of a Carboxy Terminated Branched Polyester

Mercaptoacetic acid (92.1 g, 1.0 mol) was charged to the reaction flask. AIBN (400 mg) was dissolved in trimethylolpropane diallyl ether (107 g, 0.50 mol) and the solution was slowly added to the reaction flask to keep the temperature at 80° C. When the addition was completed, heptane was added and the temperature was raised to 130° C. The condensation was followed by collection of water. The end product was a viscous syrup.

Example 11

Synthesis of a Saturated Polyurethane Dispersion

IPDI (243 g) was added to the reaction flask and heated to 80° C. A solution of GALA (43.9 g), Neopentyl glycol (26.7 g), trimethylolpropane (2.35 g), a saturated polyesterdiol (232 g, 1010 g/mol), and diacetone alcohol (75 g) was prepared and added to the reaction flask at such a rate that the temperature was kept at 80° C. When the isocyanate content had reached 5.3%, triethylamine (16.8 g) was added, and then the reaction mixture was added, with stirring to water (735 g). 1,2-ethylene diamine (20.6 g) in water (62 g) was slowly added to the dispersion to increase the molecular weight. The particle size was $Z_{ave}$ 65 nm.

Example 12

Synthesis of a Polyurethane Acrylate by Post Swelling

The dispersion of example 11 (350 g) was added to a reaction flask under nitrogen. A mixture of methyl methacrylate (78.4 g) and butyl acrylate (40.6 g) was slowly added with stirring. The radical polymerization was initiated by addition of Fe-EDTA (2.49 g, 5 mM), ascorbic acid (4.23 g, 1% aqueous solution), and t-butyl hydroperoxide. The reaction mixture was brought to 60° C. and kept there for 30 nm. Hydrogen peroxide (5.46 g, 30%) was added and the oxidation was affected at 60° C. for 30 min. The pH was reduced to 5.48 by slow addition of acetic anhydride (1 g) in diacetone alcohol (5.5 g). The particle size was $Z_{ave}$ 72 nm. Three drops of the dispersion was added to an aqueous buffer of pH 4. No aggregation was detectable, demonstrating good stability at acidic pH.

Example 13

Synthesis of a Polyurethane Acrylate by the Acrylate Solvent Method

IPDI (262 g) was added to a reaction flask under dry air and heated to 80° C. A mixture of GALA (54.2 g), Neopentyl glycol (13.0 g), trimethylolpropane (3.05 g), a saturated polesterdiol (269 g, 1027 g/mol), methyl methacrylate (178.54 g), and p-methoxyphenol (250 mg) was prepared and added to the reactor to keep the temperature at 80° C. When the isocyanate content was 5.76%, triethylamine (23.0 g) was added and the mixture was added to water (2149 g) with stirring. To the dispersion was added 1,2-ethylene diamine (28.1 g) in water (84 g). The dispersion (850 g) was then transferred to a new reaction flask and purged with nitrogen. A mixture of diacetoneacrylamide (7.56 g), maleic anhydride (1.4 g), methyl methacrylate, (71 g), and butyl acrylate (55.5 g) was added slowly. The radical polymerization was initiated by addition of Fe-EDTA (10.5 g, 5 mM), ascorbic acid (6.3 g, 1%), and t-butylhydroperoxide (105 mg). The reaction mixture was kept at 60° C. for 1 h. Then, hydrogen peroxide was added (9.26 g, 30%) to give a dispersion of pH 6.07 and particle size $Z_{ave}$ 88 nm.

Example 14

Synthesis of an Acrylated Polyurethane for Radiation Curing

An acrylated polyester was prepared from acrylic acid (133.6 g, 1.85 mol), adipic acid (135.2 g, 0.92 mol), hexanediol (208.2 g, 1.76 mol), and trimethylolpropane (89.44, 0.67 mol). The components were mixed in a reaction flask, equipped with a Dean-Stark trap for removal of reaction water. Heptane (200 g), p-toluenesulfonic acid (2.87 g), methylhydroquinone (1.57 g), and 2,6-di-t-butylcresol (0.55 g) was added and the mixture heated to reflux. When the calculated amount of water had been removed, heptane was removed by reducing the pressure. The acrylated polyester (166.1 g), a caprolactone hydroxyethyl acrylate adduct (1:1, 57.8 g), GALA (51.3 g), and triethylamine were mixed in a reaction flask and IPDI (177.7 g) was slowly added to keep the temperature between 60-80° C. When all IPDI had been added and the isocyanate number was 2.2%, the reaction mixture was dispersed in water, (40° C., 622 g), and an aqueous solution of ethylenediamine in water (40%, 20 g) was slowly added. A film was made from the dispersion and cured by UV light using Irgacure 1173. The film had ethanol/water 1:1 resistance of 300 rubs.

Example 15 pKa Values pKa values were determined by dissolving the hydroxysulphureous acid (approx. 1-2 mmol) in water (30 ml) and recording the pH as a function of volume of added aqueous potassium hydroxide (0.1 M). The pKa value was taken as the pH at ½-equivalent volume of potassium hydroxide and corrected against a standard curve prepared from measurements on maleic acid, succinic acid, methacrylic acid, propanoic acid and pentanoic acid.

TABLE 1

| Acid | pKa | Type |
| --- | --- | --- |
| DMPA* | 4.64 | regular carboxylic acid, comparative example |
| DMBA** | 4.55 | regular carboxylic acid, comparative example |
| GALA, Ex 1 | 3.67 | a hydroxysulphureous acid according to the invention |
| GAMA, Ex 5 | 3.60 | a hydroxysulphureous acid according to the invention |
| APMA, Ex 6 | 3.60 | a hydroxysulphureous acid according to the invention |
| GAPA, Ex 7 | 4.45 | a hydroxysulphureous acid according to the invention |

*DMPA is 2,2-bis-(hydroxymethyl)propanoic acid
**DMBA is 2,2-bis-(hydroxymethyl)butanoic acid

Example 16

Effect of Oxidation of Thioether Sulphur of the Hydroxysulphureous Acids

Five aqueous (35 ml) solutions of GALA (approx 2 mmol) was prepared) and varying amounts of hydrogen peroxide (0.82-2.17 eq., 30%) added. The average pKa value of the oxidation products was assessed after 2 days at room temperature, and the relation between pKa and mol ratio $H_2O_2/S$ can be seen in FIG. 1.

Thus, by addition of hydrogen peroxide, the pKa value can be reduced by approximately 1 unit with a further increase in dispersion/emulsion stability at low pH.

Example 17

Synthesis of a Polyurethane Acrylate Dispersion Using N-Ethylpyrrolidone (NEP) as Solvent IPDI (223.3 g) was added to the reaction flask and heated to 80° C. A mixture of NEP (91.8 g), GALA (43.8 g), an aliphatic polycarbonate (Mw 1000 u, 117.23 g), neopentylglycol (12.2 g), trimethylolpropane (2.25 g), an aliphatic polyester (Mw 1000 u, 117.2 g) was added slowly to the reaction flask to keep the temperature between 80-85° C. When all reactants had been added and the NCO number was approximately 6.2, the mixture was slowly added to water (1017 g) followed by addition of 1,5-diamino-2-methylpentane (44.5 g in water (70 g)) to complete a dispersion of high stability at low pH. Optionally, the dispersion can be made even more stabile by the addition of hydrogen peroxide.

Example 18

Synthesis of a Polyurethane Acrylate Dispersion Using a Naturally Renewable Polyester IPDI (223.3 g) was added to the reaction flask and heated to 80° C. A mixture of methyl methacrylate (91.8 g), GALA (43.8 g), a dimerized fatty acid polyester (Mw 1000 u, 117.23 g), neopentylglycol (12.2 g), trimethylolpropane (2.25 g), an aliphatic polyester (Mw 1000 u, 117.2 g) was added slowly to the reaction flask to keep the temperature between 80-85° C. When all reactants had been added and the NCO number was approximately 6.2, the mixture was slowly added to water (1017 g) followed by addition of diaminoethane (23.3 g in water (70 g)). The methyl methacrylate was polymerized by addition of sodium peroxodisulfate (650 mg in 50 ml water) and sodium pyrosulfite (500 mg in 50 ml water) at 40° C. The thioethers of the product were oxidised by addition of hydrogen peroxide (30%, 38 g).

Example 19

Synthesis of a Polyurethane Acrylate Dispersion Using Soft Building Blocks

IPDI (223.3 g) was added to the reaction flask and heated to 80° C. A mixture of NEP (91.8 g), GALA (43.8 g), a polytetrahydrofuranediol (Mw 1000 u, 117.23 g), 2,2,6,6-tetrakis(hydroxymethyl)cyclohexanol (15.6 g), an aliphatic polyester (Mw 1000 u, 117.2 g) was added slowly to the reaction flask to keep the temperature between 80-85° C. When all reactants had been added and the NCO number was 6.26, the mixture was slowly added to water (1017 g) followed by addition of adipic acid dihydrazide (66.1 g in water (70 g)) to complete a dispersion of high stability at low pH. The thioethers of the product were oxidised by addition of hydrogen peroxide (30%, 38 g).

The invention claimed is:

1. A hydroxysulphureous acid comprising the general formula I

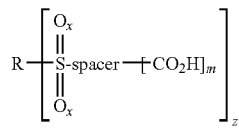

wherein z is an integer from 1 to 3,
wherein m is an integer from 1 to 3,
wherein each x independently is an integer from 0 to 1,
wherein spacer comprises branched or linear aliphatic carbon chains, and/or alicyclic and/or aromatic carbon rings, each optionally comprising oxygen, nitrogen, sulphur or halogens, and
wherein R is selected from the group consisting of:

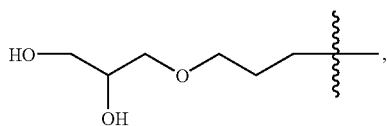

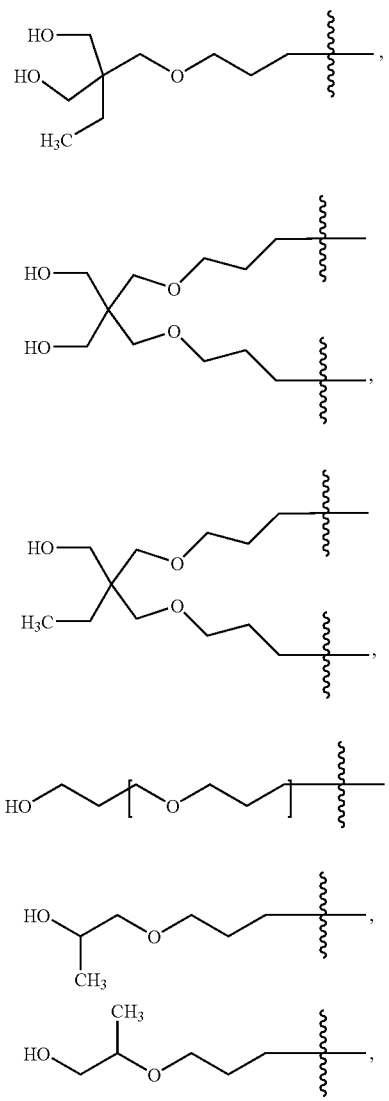

or a polymer having at least one terminal hydroxy group and a molecular weight below 2000, wherein said polymer is a polyester selected from the group consisting of a fatty acid ester, an unsaturated ester, an alkyd or an allylether polyester;

or a salt of said hydroxysulphureous acid.

2. The hydroxysulphureous acid according to claim 1, wherein said spacer is a linear or branched alkyl chain comprising 1-10 carbon atoms.

3. The hydroxysulphureous acid according to claim 2, wherein said spacer is spacer is selected from methylene or ethylene.

4. The hydroxysulphureous acid of claim 1, obtainable by addition of a mercaptocarboxylic compound to a hydroxyalkene or epoxide.

5. The hydroxysulphureous acid according claim 4, wherein the mercaptocarboxylic compound is an aliphatic or aromatic mercaptocarboxylic acid;

the hydroxyalkene is an unsaturated alcohol, an unsaturated polyester, or a fatty acid ester.-

6. The hydroxysulphureous acid according to claim 1, represented by the general formula II:

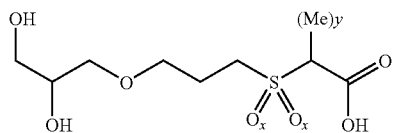

wherein each x and y independently is 0 or 1.

7. The hydroxysulphureous acid according to claim 1, represented by the general formula III:

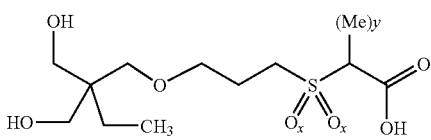

wherein each x and y independently is 0 or 1.

8. The hydroxysulphureous acid according to claim 1, represented by the general formula IV:

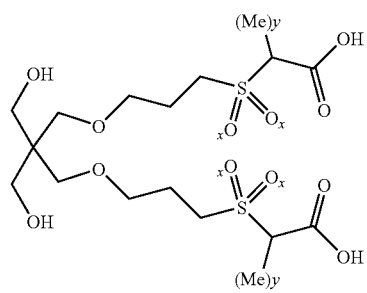

wherein each x and each y independently is 0 or 1.

9. The hydroxysulphureous acid according to claim 1, represented by the general formula V:

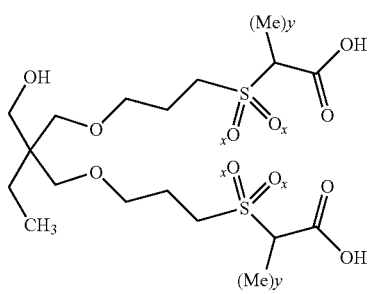

wherein each x and each y independently is 0 or 1.

10. The hydroxysulphureous acid according to claim 1, represented by any one of the formulas:

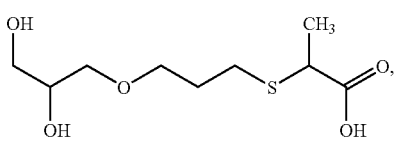

-continued

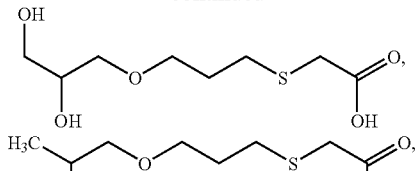

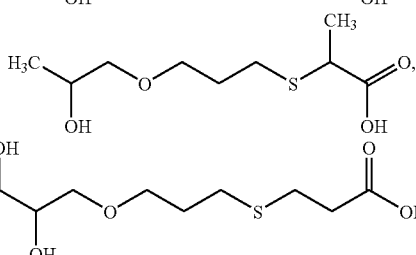

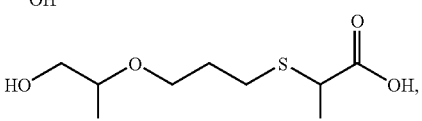

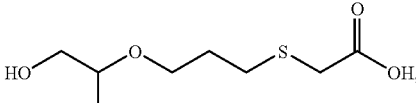

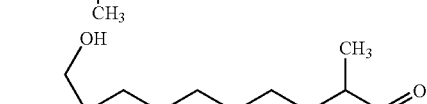

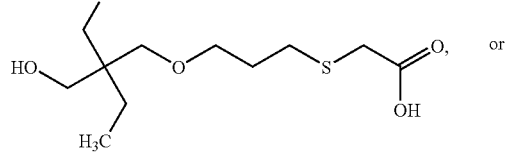

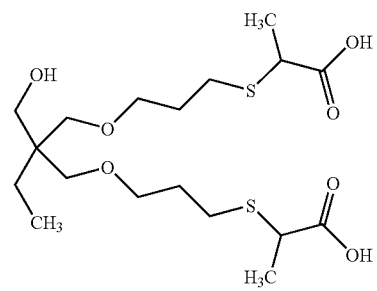 [SMILES: CCC(CO)(COCCCSC(C)C(=O)O)COCCCSC(C)C(=O)O]

wherein each sulphur atom optionally is oxidised to a sulphoxide or sulphone.

11. The hydroxysulphureous acid of claim 1, wherein the sulphur atom in formula I is oxidised to a sulphoxide or sulphone.

12. A method for producing the hydroxysulphureous acid of claim 1, wherein said method comprises:
   a) providing a mercaptocarboxylic compound or a salt thereof,
   b) providing a hydroxyalkene or an epoxide, and
   c) reacting the mercaptocarboxylic compound with the hydroxyalkene or the epoxide,
wherein said hydroxysulphureous acid is obtained.

13. The method of claim 12, wherein the mercaptocarboxylic compound is an aliphatic or aromatic mercaptocarboxylic acid; and the hydroxyalkene is an unsaturated alcohol, an unsaturated polyester, or a fatty acid derivative.

14. The method of claim 12, wherein the reaction is run
a) neat; or
b) in the presence of a solvent; or
c) in the presence of an initiator; or
d) where the reaction mixture is irradiated with electromagnetic radiation,
or any combination thereof.

15. A method for preparation of the product of a product wherein the hydroxysulphureous acid of claim 1 is reacted with an alkylene oxide, a carboxylic acid, a lactone, an acrylic acid, an acrylic ester, a methacrylic acid, a methacrylic ester, an acrylated polymer, an isocyanate, an alcohol or alkoxylated polyols to obtain said product.

16. A product, comprising an ether; a polyether; an ester; a polyester; a urethane; a polyurethane; a urethane acrylate; a polyurethane acrylate; an acrylated polyurethane or acrylated polyester for radiation curing; or any mixture thereof, which is wherein said product is prepared using the method of claim 15.

17. The product according to claim 16, comprising a polyester wherein said polyester is a linear or branched polyester.

18. A method for preparation of a product comprising: an ether; a polyether; an ester; a polyester; a urethane; a polyurethane; a urethane acrylate; a polyurethane acrylate; an acrylated polyurethane or acrylated polyester for radiation curing, wherein said product is prepared by homocondensation of the hydroxysulphureous acid of claim 1; or by co-condensation of the hydroxysulphureous acid of claim 1 with a carboxylic acid or a mixture thereof, wherein said homocondensation or said co-condensation optionally comprises including an alcohol and/or a catalyst during said preparation and wherein said product formed by said homocondensation or said co-condensation is optionally chain extended, chain terminated and/or functionalised.

19. A method for preparing a urethane product comprising reacting:
a) an isocyanate or an isocyanate mixture,
b) a polyol,
c) the hydroxysulphureous acid of claim 1, and
d) a neutralising base or a mixture of neutralising bases to provide a urethane or polyurethane.

20. The method of claim 19, further comprising adding an acrylic ester to the urethane or polyurethane, followed by polymerization of the acrylic ester.

21. A method of coating a substrate comprising coating a substrate selected from the group consisting of wood substrates, metal substrates, leather substrates, textile substrates, plastic substrates and paper substrates with the product of claim 15.

22. The method of claim 21 further comprising radiation curing, wherein the product is a polyurethane; a urethane acrylate; a polyurethane acrylate; an acrylated polyurethane or acrylated polyester; or any mixture thereof, wherein the substrate is a wood substrate, wherein said wood substrate is wooden tile and/or parquet flooring.

23. A method of preparing a coating, printing ink, or adhesive comprising radiation curing said printing ink or adhesive comprising a product of claim 15, wherein said product is a acrylated polyurethane or acrylated polyester.

24. A product comprising the polyester of claim 16, wherein said product is selected from the group consisting of:
a) an air drying alkyd resin,
b) a 1- or 2-component polyurethane coating or adhesive,
c) a saturated or unsaturated polyester,
d) a toughening agent for thermosetting resins and/or composites made therefrom,
e) a pigment dispersion agent for solvent-free, solvent-borne, waterborne coatings, polyolefines and thermoplastics,
f) a water dispersible resin for alkyd emulsions, acrylic dispersions and polyurethane dispersions,
g) a dispersing polymer or resin,
h) a processing aid for polyolefines and thermoplastics,
i) a concrete admixture imparting fluidity to hydraulic compositions, or
j) a polyurethane foam.

25. A method of preparing a coating, printing ink, or adhesive comprising radiation curing said printing ink or adhesive comprising an acrylated polyester of claim 15.

26. The method of claim 12, further comprising oxidising the sulphur atom of the hydroxysulphureous acid to a sulphoxide or a sulphone.

27. The method of claim 13, wherein the unsaturated alcohol is an allyl alcohol or an allyl alcohol derivative.

28. The method of claim 12, wherein the unsaturated polyester is an alkyd or a maleic acid polyester or an allyl ether polyester.

29. An alkyd emulsion comprising the product of claim 15, wherein said product is a polyester.

30. An aqueous mixture comprising the product of claim 15, wherein said product is a polyurethane.

31. The method of claim 19, wherein said reacting occurs in the presence of at least one agent selected from the group consisting of 2,2-bis(hydroxymethyl)propanoic acid, 2,2-bis(hydroxymethyl)butanoic acid, hydroxypivalic acid, a catalyst or a mixture of catalysts, a solvent or a mixture of solvents, additives, a chain extending nitrogen compound or a mixture of nitrogen compounds, an oxidising agent, and a pH adjuster.

32. The method of claim 19, wherein said reacting occurs in the presence of at least one agent selected from the group consisting of a catalyst or a mixture of catalysts, and a chain extending nitrogen compound or a mixture of nitrogen compounds.

33. The hydroxysulphureous acid of claim 5, wherein the unsaturated alcohol is an allyl alcohol or an allyl alcohol derivative.

34. The hydroxysulphureous acid of claim 5, wherein the unsaturated polyester is an alkyd or a maleic acid polyester or an allyl ether polyester.

35. The method of claim 17 wherein said lactone is caprolactone.

36. A method for preparing an acrylated polyester by acrylating the polyester of claim 16 with acrylic acid, acrylic ester, methacrylic acid or methacrylic ester.

37. A hydroxysulphureous acid comprising the general formula I

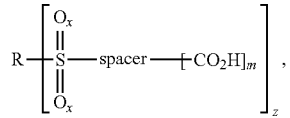

wherein:
z is an integer from 1 to 3;
m is an integer from 1 to 3;
each x independently is an integer from 0 to 1;

spacer comprises branched or linear aliphatic carbon chains, and/or alicyclic and/or aromatic carbon rings, each optionally comprising oxygen, nitrogen, sulphur, or halogen; and R is selected from the group consisting of:

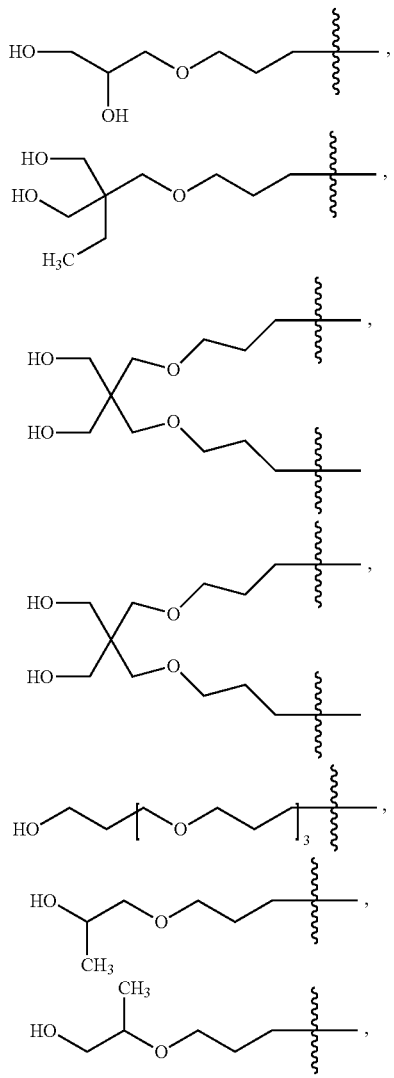

or salts thereof.

38. The hydroxysulphureous acid of claim 1, wherein R is selected from the group consisting of:

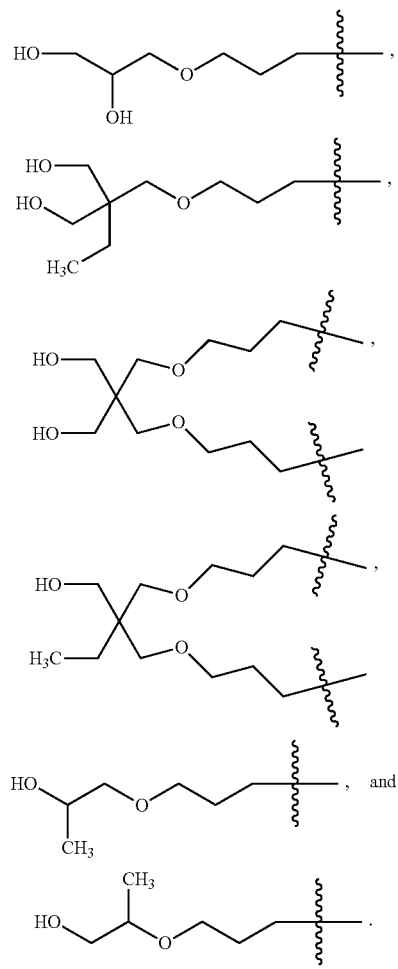

39. The method of claim 18, wherein said method further comprises including an alcohol and/or a catalyst during said preparation.

40. The method of claim 18, wherein said product is chain extended, chain terminated and/or functionalized.

* * * * *